United States Patent
Brown et al.

(10) Patent No.: US 6,946,463 B2
(45) Date of Patent: Sep. 20, 2005

(54) 1,2,5,10-TETRAHYDROPYRIDAZINO[4,5-B] QUINOLINE-1,10-DIONES AND THEIR USE FOR THE TREATMENT OF PAIN

(75) Inventors: Dean Gordon Brown, Wilmington, DE (US); Rebecca Ann Urbanek, Wilmington, DE (US); Megan Murphy, Wilmington, DE (US); Wenhua Xiao, Wilmington, DE (US); Frances Marie McLaren, Wilmington, DE (US); Edward Vacek, Wilmington, DE (US); Thomas Bare, West Chester, PA (US); Carey Lynn Horchler, Wilmington, DE (US); Christine Barlaam, Reims (FR); Gary Banks Steelman, Wilmington, DE (US)

(73) Assignee: Astrazeneca AB, Sodertalje (SE)

( * ) Notice: Subject to any disclaimer, the term of this patent is extended or adjusted under 35 U.S.C. 154(b) by 97 days.

(21) Appl. No.: 10/381,921

(22) PCT Filed: Sep. 28, 2001

(86) PCT No.: PCT/SE01/02126

§ 371 (c)(1),
(2), (4) Date: Sep. 8, 2003

(87) PCT Pub. No.: WO02/26741

PCT Pub. Date: Apr. 4, 2002

(65) Prior Publication Data

US 2004/0053929 A1 Mar. 18, 2004

Related U.S. Application Data

(60) Provisional application No. 60/236,880, filed on Sep. 29, 2000.

(51) Int. Cl.[7] .................. A61K 31/5025; C07D 471/04
(52) U.S. Cl. ...................................... 514/248; 544/234
(58) Field of Search ........................... 544/234; 514/248

(56) References Cited

U.S. PATENT DOCUMENTS

2003/0153571 A1 * 8/2003 Brown et al. ............... 514/248

2003/0162783 A1 * 8/2003 Alford et al. ............... 514/248
2004/0053930 A1 * 3/2004 Brown et al. ............... 514/248

FOREIGN PATENT DOCUMENTS

| EP | 0736531 | 10/1996 |
|----|---------|---------|
| WO | WO 9511244 | 4/1995 |
| WO | WO 0147523 | 7/2001 |
| WO | WO 0147524 | 7/2001 |
| WO | WO 0147923 | 7/2001 |
| WO | WO 0147924 | 7/2001 |
| WO | WO 0147925 | 7/2001 |
| WO | 2002/026740 | * 4/2002 |

* cited by examiner

Primary Examiner—Emily Bernhardt
(74) Attorney, Agent, or Firm—Kenneth F. Mitchell

(57) ABSTRACT

Compounds according to structural diagram (I)

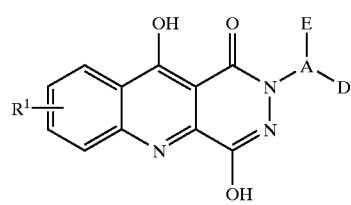

are disclosed, wherein $R^1$, A, E and D are as defined in the specification. Also disclosed are pharmaceutical compositions comprising a pain-ameliorating effective amount of a compound in accord with structural diagram (I).

The following is an examiner's statement of reasons for allowance: In view of applicants' amendments to the claims which limit "E" to phenyl or cycloalkyl groups the rejections of the previous action no longer pertain as they at best teach "E" as alkyl.

8 Claims, No Drawings

1,2,5,10-TETRAHYDROPYRIDAZINO[4,5-B] QUINOLINE-1,10-DIONES AND THEIR USE FOR THE TREATMENT OF PAIN

This is the National Stage of International Application PCT/SE01/02126, filed Sep. 28, 2001, which claims priority under 35 U.S.C. §119(e) of U.S. Provisional Applications 60/171,906, filed Dec. 23, 1999 and 60/236,880, filed Sep. 29, 2000.

FIELD OF THE INVENTION

This invention relates to the treatment or prevention of pain or nociception.

RELATED ART

Pain is a sensory experience distinct from sensations of touch, pressure, heat and cold. It is often described by sufferers by such terms as bright, dull, aching, pricking, cutting or burning and is generally considered to include both the original sensation and the reaction to that sensation. This range of sensations, as well as the variation in perception of pain by different individuals, renders a precise definition of pain difficult, however, many individuals suffer with severe and continuous pain.

Pain that is caused by damage to neural structures is often manifest as a neural supersensitivity or hyperalgesia and is termed "neuropathic" pain. Pain can also be "caused" by the stimulation of nociceptive receptors and transmitted over intact neural pathways, such pain is termed "nociceptive" pain.

The level of stimulation at which pain becomes noted is referred to as the "pain threshold." Analgesics are pharmaceutical agents which relieve pain by raising the pain threshold without a loss of consciousness. After administration of an analgesic drug a stimulus of greater intensity or longer duration is required before pain is experienced. In an individual suffering from hyperalgesia an analgesic drug may have an anti-hyperalgesic effect. In contrast to analgesics, agents such as local anaesthetics block transmission in peripheral nerve fibers thereby blocking awareness of pain. General anaesthetics, on the other hand, reduce the awareness of pain by producing a loss of consciousness.

Tachykinin antagonists have been reported to induce antinociception in animals, which is believed to be analogous to analgesia in man (Maggi et al, J. Auton. Pharmacol. (1993) 13, 23–93). In particular, non-peptide NK-1 receptor antagonists have been shown to produce such analgesia. For example, the NK-1 receptor antagonist RP 67,580 produced analgesia with potency comparable to that of morphine (Garret et al, Proc. Natl. Acad. Sci. USA (1993) 88, 10208–10212).

The opioid analgesics are a well-established class of analgesic agents with morphine-like actions. Synthetic and semi-synthetic opioid analgesics are derivatives of five chemical classes of compound: phenanthrenes; phenylheptylamines; phenylpiperidines; morphinans; and benzomorphans. Pharmacologically these compounds have diverse activities, thus some are strong agonists at the opioid receptors (e.g. morphine); others are moderate to mild agonists (e.g. codeine); still others exhibit mixed agonist-antagonist activity (e.g. nalbuphine); and yet others are partial agonists (e.g. nalorphine). Whilst an opioid partial agonist such as nalorphine, (the N-alkyl analogue of morphine) will antagonize the analgesic effects of morphine, when given alone it can be a potent analgesic in its own right.

Of all of the opioid analgesics, morphine remains the most widely used, but, in addition to its therapeutic properties, it has a number of drawbacks including respiratory depression, decreased gastrointestinal motility (resulting in constipation), nausea and vomiting. Tolerance and physical dependence also limit the clinical uses of opioid compounds.

Aspirin and other salicylate compounds are frequently used in treatment to interrupt amplification of the inflammatory process in rheumatoid diseases and arthritis and temporarily relieve the pain. Other drug compounds used for these purposes include phenylpropionic acid derivatives such as Ibuprofen and Naproxen, Sulindac, phenyl butazone, corticosteroids, antimalarials such as chloroquine and hydroxychloroquine sulfate, and fenemates (J. Hosp. Pharm., 36:622 (May 1979)). These compounds, however, are ineffective for neuropathic pain.

Available therapies for pain also have drawbacks. Some therapeutic agents require prolonged use before an effect is experienced by the patient. Other existing drugs have serious side effects in certain patients, and subjects must be carefully monitored to ensure that any side effects are not unduly threatening. Most existing drugs provide only temporary relief from pain and must be taken consistently on a daily or weekly basis. With disease progression the amount of medication needed to alleviate the pain often increases, thus increasing the potential for adverse side effects.

NMDA receptors are defined by the binding of N-methyl-D-aspartate (NMDA) comprise a receptor/ion channel complex with several different identified binding domains. NMDA itself is a molecule structurally similar to glutamate (Glu) which binds at the glutamate binding suite and is highly selective and potent in activating the NMDA receptor (Watkins (1987); Olney (1989)).

Many compounds are known that bind at the NMDA/Glu binding site (for example CPP, DCPP-ene, CGP 40116, CGP 37849, CGS 19755, NPC 12626, NPC 17742, D-AP5, D-AP7, CGP 39551, CGP-43487, MDL-100,452, LY-274614, LY-233536, and LY233053). Other compounds, referred to as non-competitive NMDA antagonists, bind at other sites in the NMDA receptor complex (examples are phencyclidine, dizocilpine, ketamine, tiletamine, CNS 1102, dextromethorphan, memantine, kynurenic acid, CNQX, DNQX, 6,7-DCQX, 6,7-DCHQC, R(+)-HA-966, 7-chloro-kynurenic acid, 5,7-DCKA, 5-iodo-7-chloro-kynurenic acid, MDL-28,469, MDL-100,748, MDL-29,951, L-689,560, L-687,414, ACPC, ACPCM, ACPCE, arcaine, diethylenetriamine, 1,10-diaminodecane, 1,12-diaminododecane, ifenprodil, and SL-82.0715). These compounds have been extensively reviewed by Rogawski (1992) and Massieu et. al., (1993), and articles cited therein.

In addition to its physiological function, glutamate (Glu) can be neurotoxic. Glu neurotoxicity is referred to as "excitotoxicity" because the neurotoxic action of Glu, like its beneficial actions, is mediated by an excitatory process (Olney (1990); Choi (1992)). Normally, when Glu is released at a synaptic receptor, it binds only transiently and is then rapidly removed from the receptor by a process that transports it back into the cell. Under certain abnormal conditions, including stroke, epilepsy and CNS trauma, Glu uptake fails and Glu accumulates at the receptor resulting in a persistent excitation of electrochemical activity that leads to the death of neurons that have Glu receptors. Many neurons in the CNS have Glu receptors, so excitotoxicity can cause an enormous amount of CNS damage.

Acute excitotoxicity injury can occur as a result of ischemic events, hypoxic events, trauma to the brain or spinal cord, certain types of food poisoning which involve an excitotoxic poison such as domoic acid, and seizure-mediated neuronal degeneration, which can result from persistent epileptic seizure activity (status epilepticus). A large body of evidence has implicated the NMDA receptor as one receptor subtype through which Glu mediates a substantial amount of CNS injury, and it is well established that NMDA antagonists are effective in protecting CNS neurons against excitotoxic degeneration in these acute CNS injury syndromes (Choi (1988); Olney (1990)).

In addition to neuronal damage caused by acute insults, excessive activation of Glu receptors may also contribute to more gradual neurodegenerative processes leading to cell death in various chronic neurodegenerative diseases, including Alzheimer's disease, amyotrophic lateral sclerosis, AIDS dementia, Parkinson's disease and Huntington's disease (Olney (1990)). It is generally considered that NMDA antagonists may prove useful in the therapeutic management of such chronic diseases.

In the 1980's it was discovered that PCP (also known as "angel dust") acts at a "PCP recognition site" within the ion channel of the NMDA Glu receptor. PCP acts as a non-competitive antagonist that blocks the flow of ions through the NMDA ion channel. More recently it has become evident that drugs which act at the PCP site as non-competitive NMDA antagonists are likely to have psychotomimetic side effects. Further, it is now recognized that certain competitive and non-competitive NMDA antagonists can cause similar pathomorphological effects in rat brain (Olney et. al., (1991); Hargreaves et. al., (1993)). Such compounds also have psychotomimetic effects in humans (Kristensen et. al., (1992); Herrling (1994); Grotta (1994)).

The glycine binding site of the NMDA receptor complex is distinguishable from the Glu and PCP binding sites. Also, it has recently been discovered that NMDA receptors occur as several subtypes which are characterized by differential properties of the glycine binding site of the receptor. Many compounds that bind at the NMDA receptor glycine site, useful for the treatment of stroke and neurodegenerative conditions, have been described in U.S. Pat. Nos. 5,604,227; 5,733,910; 5,599,814; 5,593,133; 5,744,471; 5,837,705 and 6,103,721.

SUMMARY OF THE INVENTION

It has now been discovered that certain compounds which exhibit the property of binding to the NMDA receptor glycine site have utility for the amelioration of pain and particularly for the amelioration of neuropathic pain.

In a first aspect the invention provides compounds according to structural diagram I useful for the treatment of pain,

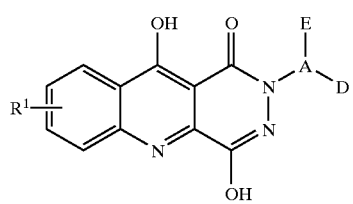

wherein: $R^1$ is halo; A is CH; E is selected from $C_{1-4}$alkyl, phenyl and $C_{3-7}$cycloalkyl, and D is selected from pyridyl and N-oxide of pyridyl.

Other compounds useful in the methods and compositions of the invention are pharmaceutically-acceptable salts of the compounds in accord with structural diagram I and tautomers of such a compounds.

Particular compounds of the invention are those wherein E is selected from methyl, phenyl and $C_{3-5}$cycloalkyl.

More particular compounds of the invention are those according to structural diagram II:

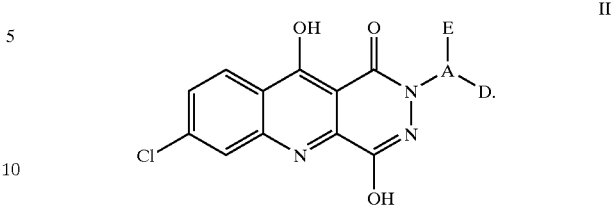

Still more particular compounds of the invention are those wherein E is selected from methyl, phenyl and $C_{3-5}$cycloalkyl.

The most particular embodiments of the invention are those exemplary compounds specifically disclosed herein.

In another aspect the invention provides a method for the treatment of pain comprising administering a pain-ameliorating effective amount of any compound according to structural diagram I as heretofore defined.

In particular embodiments the method comprises administering pain-ameliorating effective amounts of compounds according to structural diagram I wherein: E is selected from methyl, phenyl and $C_{3-5}$cycloalkyl.

In further particular embodiments the method comprises administering pain-ameliorating effective amounts of compounds according to structural diagram II wherein: E is selected from methyl, phenyl and $C_{3-5}$cycloalkyl.

Yet another aspect of the invention is a pharmaceutical composition comprising a pain-ameliorating effective amount of a compound according to structural diagram I:

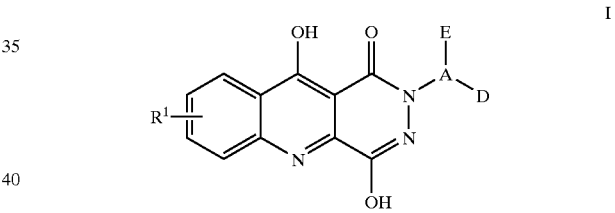

wherein: $R^1$ is halo; A is CH; E is selected from $C_{1-4}$alkyl, phenyl and $C_{3-7}$cycloalkyl; D is selected from pyridyl and N-oxide of pyridyl, or tautomers or pharmaceutically-acceptable salts thereof together with a pharmaceutically-acceptable excipient or diluent.

Still more particular embodiments of the invention are those where the method comprises treatment with an exemplary compound specifically disclosed herein.

Yet other aspects of the invention are pharmaceutical compositions which contain a compound in accord with structural diagram I; the use of compounds in accord with structural diagram I for the preparation of medicaments and pharmaceutical compositions, and a method comprising binding a compound of the invention to the NMDA receptor glycine site of a warm-blooded animal, such as a human being, so as to beneficially inhibit the activity of the NMDA receptor.

DETAILED DESCRIPTION OF THE INVENTION

Compounds of the invention are those within the scope of the generic description and particularly those compounds exemplified hereafter.

Suitable pharmaceutically-acceptable salts of compounds of the invention include acid addition salts such as methanesulphonate, fumarate, hydrochloride, hydrobromide, citrate, tris(hydroxymethyl)aminomethane, maleate and salts formed with phosphoric and sulphuric acid. In other embodiments, suitable salts are base salts such as an alkali metal salts for example sodium, alkaline earth metal salts for example calcium or magnesium, organic amine salts for example triethylamine, morpholine, N-methylpiperidine, N-ethylpiperidine, procaine, dibenzylamine, choline, N,N-dibenzylethylamine or amino acids such as lysine.

Another aspect of the invention is a process for making compounds of the invention, which process comprises the following steps:

Another aspect of the invention is a process for making compounds of the invention, which process comprises the following steps:

a) Preparing a ketone by reacting a nitrile in the presence of a Grignard reagent, followed by acidic work-up according to the following scheme to form said ketone:

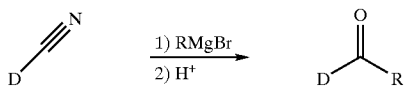

where R is an alkyl group;

b) preparing a Boc-protected hydrazine by reacting a ketone as prepared in step a), or an aldehyde, according to one of the procedures shown in the following scheme:

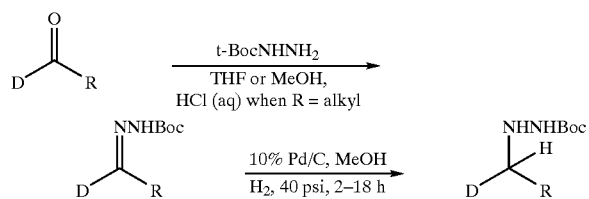

c) coupling said Boc-protected hydrazine and cyclizing the product according to the process of the following scheme to form a compound according to structural diagram I:

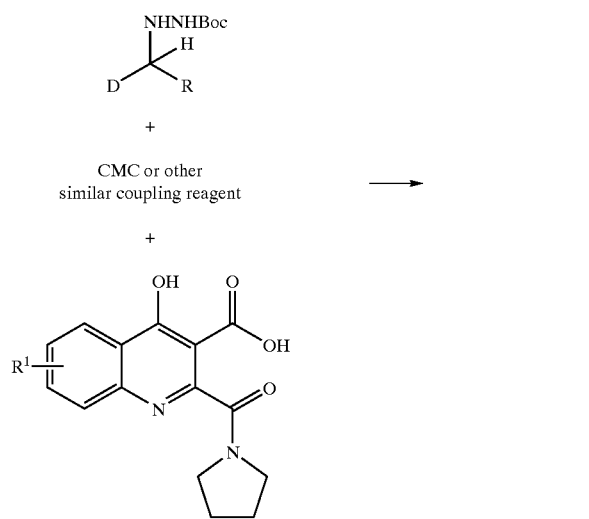

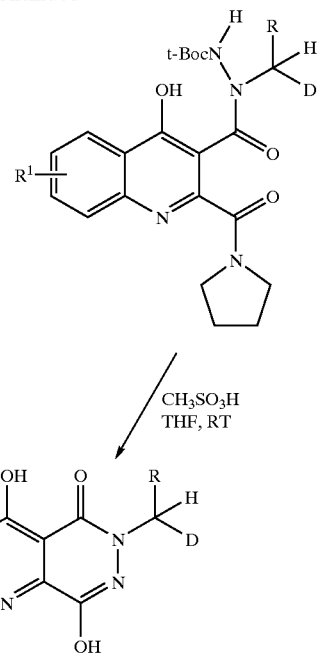

wherein:

CMC is 1-cyclohexyl-3-(2-morpholinoethyl) carbodiimide metho-p-toluenesulfonate;

the "R/H/D" group is the "A-D-E" moiety of structural diagram I, and throughout the foregoing process $R^1$ is as defined for structural diagram I.

To use a compound of the invention or a pharmaceutically-acceptable salt thereof for the therapeutic treatment, which may include prophylactic treatment, of pain in mammals, which may be humans, the compound can be formulated in accordance with standard pharmaceutical practice as a pharmaceutical composition.

Suitable pharmaceutical compositions that contain a compound of the invention may be administered in conventional ways, for example by oral, topical, parenteral, buccal, nasal, vaginal or rectal administration or by inhalation. For these purposes a compound of the invention may be formulated by means known in the art into the form of, for example, tablets, capsules, aqueous or oily solutions, suspensions, emulsions, creams, ointments, gels, nasal sprays, suppositories, finely divided powders or aerosols for inhalation, and for parenteral use (including intravenous, intramuscular or infusion) sterile aqueous or oily solutions or suspensions or sterile emulsions. A preferred route of administration is orally by tablet or capsule.

In addition to a compound of the present invention a pharmaceutical composition of this invention may also contain one or more other pharmacologically-active agents, or such pharmaceutical composition may be simultaneously or sequentially co-administered with one or more other pharmacologically-active agents.

Pharmaceutical compositions of this invention will normally be administered so that a pain-ameliorating effective daily dose is received by the subject. The daily dose may be given in divided doses as necessary, the precise amount of the compound received and the route of administration depending on the weight, age and sex of the patient being treated and on the particular disease condition being treated according to principles known in the art. A preferred dosage regime is once daily.

A further embodiment of the invention provides a pharmaceutical composition which contains a compound of the structural diagram I as defined herein or a pharmaceutically-acceptable salt thereof, in association with a pharmaceutically-acceptable additive such as an excipient or carrier.

A yet further embodiment of the invention provide the use of a compound of the structural diagram I, or a pharmaceutically-acceptable salt thereof, in the manufacture of a medicament useful for binding to the NMDA receptor glycine site in a warm-blooded animal such as a human being.

Still another embodiment of the invention provides a method of binding a compound of the invention to the NMDA receptor-glycine site of a warm-blooded animal, such as a human being, in need of treatment for pain, which method comprises administering to said animal an effective amount of a compound of structural diagram I or a pharmaceutically-acceptable salt thereof.

Definitions:

When used herein the term "alkyl" includes both straight and branched chain alkyl groups but references to individual alkyl groups such as "propyl" refer to the straight chain moiety.

When used herein the term "halo" means fluoro, chloro, bromo and iodo.

Generally in the methods, processes and examples described herein:

concentrations were carried out by rotary evaporation in vacuo;

operations were carried out at ambient temperature, that is in the range 18–26° C. and under a nitrogen atmosphere;

column chromatography (by the flash procedure) was performed on Merck Kieselgel silica (Art. 9385) unless otherwise stated;

yields are given for illustration only and are not necessarily the maximum attainable;

the structure of the end-products of the formula I were generally confirmed by NMR and mass spectral techniques, proton magnetic resonance spectra were determined in DMSO-$d_6$ unless otherwise stated using a Varian Gemini 2000 spectrometer operating at a field strength of 300 MHz; chemical shifts are reported in parts per million downfield from tetramethylsilane as an internal standard ($\delta$ scale) and peak multiplicities are shown thus: s, singlet; bs, broad singlet; d, doublet; AB or dd, doublet of doublets; t, triplet, dt, double of triplets, m, multiplet; bm, broad multiplet; fast-atom bombardment (FAB) mass spectral data were obtained using a Platform spectrometer (supplied by Micromass) run in electrospray and, where appropriate, either positive ion data or negative ion data were collected, in this application, (M+H)$^+$ is quoted;

intermediates were not generally fully characterized and purity was in general assessed mass spectral (MS) or NMR analysis.

The following abbreviations and definitions when used, have the meanings, as follows:

CDCl$_3$ is deuterated chloroform;

CMC is 1-cyclohexyl-3-(2-morpholinoethyl) carbodiimide metho-p-toluenesulfonate;

DCM is dichloromethane;

DCU is dicyclohexyl urea;

DHC is 1,3-dicyclohexylcarbodiimide;

DMAP is 4-(dimethylamino)pyridine;

DMF is N,N-dimethylformamide;

DMSO is dimethylsulphoxide;

m/s is mass spectroscopy;

NMP is N-methylpyrrolidinone;

NMR is nuclear magnetic resonance;

p.o. is per os;

TBF is tetrahydrofuran, and t.i.d. is three times daily.

The examples and tests described herein are intended to illustrate but not limit the invention.

EXAMPLES

Example 1

(+/−)-7-Chloro-4-hydroxy-2-(1-cyclopropyl-1-pyrid-2-yl)methyl-1,2,5,10-tetrahydropyridazino[4,5-b]quinoline-1,10-dione Cyclopropyl-2-pyridyl ketone.

Dry magnesium powder (0.79 g, 32.6 mmol), which had been previously crushed in a mortar with a pestle, was charged into a dry round bottom flask under a nitrogen atmosphere. To this was added diethyl ether (20 mL), followed by bromocyclopropane (3.95 g, 2.61 mL, 32.6 mmol). A small amount of iodine (0.002 g) was added to initiate formation of the Grignard reagent. The reaction was heated to a gentle reflux for a short period of time (~1 h) until all of the magnesium metal had reacted. The material was allowed to stir at room temperature for 2 hours, and then cooled in an ice bath. To this was added 2-cyanopyridine (2.0 g, 19.2 mmol) in diethyl ether (10 mL). The mixture was stirred for 3 hours, and then carefully quenched with sat. ammonium chloride (3 mL). The reaction was then acidified with 15% aq. hydrochloric acid (3 mL). The mixture was stirred for 20 minutes, and then made basic by the addition of 10 N sodium hydroxide until the pH was approximately 9. To this solution was added ethyl acetate (300 mL), and the aqueous layer was extracted with water (30 mL). The organic layer was washed with brine, dried over Na$_2$SO$_4$ and evaporated to dryness giving a yellow oil. This oil was chromatographed (SiO$_2$, hexanes/ethyl acetate: 75/25) to give the title compound as a yellow oil (1.48 g, 52%). $^1$H NMR (300 MHz, DMSO-$d_6$): $\delta$ 1.10 (m, 4H); 3.46 (m, 1H); 7.70 (m, 1H); 7.96 (t, 1H, J=78. Hz); 8.01 (t, 1H, J=7.8 Hz); 8.77 (d, 1H, J=4.8 Hz).

N-1-Aza-2-cyclopropyl-2-(2-pyridyl)vinyl)(tert-butoxy)carboxamide.

To a stirred solution of tert-butylcarbazate (1.32 g, 10.0 mmol) in THF (50 mL) was added cyclopropyl-2-pyridyl ketone (1.48 g, 10.0 mmol), followed by 3 drops of concentrated hydrochloric acid. The reaction was stirred overnight and the solvent removed in vacuo. The resultant solid was triturated with hexanes to give the title compound as a white solid (1.90 g, 72%). $^1$H NMR (300 MHz, DMSO-$d_6$): $\delta$ 0.86 (m, 4H); 1.45 (s, 9H); 2.03 (m, 1H); 7.54 (m, 1H); 8.07 (m, 2H); 8.73 (m, 1H); 13.42 (br s, 1H).

(+/−)-(tert-butoxy)-N-[(cyclopropyl-2-pyridylmethyl)amino]carboxamide.

N-1-Aza-2-cyclopropyl-2-(2-pyridyl)vinyl)(tert-butoxy)carboxamide (1.90 g, 7.30 mmol) was dissolved in methyl alcohol (90 mL) and placed in a Parr shaker bottle. To this was added 10% palladium-on-carbon (300 mg) and the reaction was hydrogenated at 40 psi for 18 h. The catalyst was filtered on diatomaceous earth, washed with methyl alcohol (2×300 mL), and the solvents were removed in vacuo to give an oil. This oil was chromatographed (SiO$_2$, 60/40 hexanes/ethyl acetate and then ethyl acetate as eluants) to give the title compound (1.05 g, 54%) as an oil. $^1$H NMR (300 MHz, DMSO-d$_6$): δ 0.29 (m, 1H); 0.36 (m, 1H); 0.53 (m, 1H); 0.87 (m, 1H); 1.34 (s, 9H); 3.25 (br m, 1H); 4.72 (m, 1H); 7.25 (t, 1H, J=4.8, 8.1 Hz); 7.51 (d, 1H, J=8.1 Hz); 7.75 (t, 1H, J=8.1 Hz); 8.16 (br s, 1H); 8.47 (d, 1H, J=4.8 Hz).

Dimethyl 7-chloro-4-hydroxyquinoline-2,3-dicarboxylate:

A stirred mixture of methyl 2-amino-4-chlorobenzoate (2.50 g, 13.5 mmol) and dimethyl acetylenedicarboxylate (2.05 g, 14.4 mmol) in tert-butanol (22 ml) was refluxed for 7 hours under a nitrogen atmosphere. After adding additional dimethyl acetylenedicarboxylate (1.16 g, 8.13 mmol) and refluxing another 2.5 hours, the reaction mixture was allowed to cool to room temperature and potassium tert-butoxide (1.56 g, 13.9 mmol) was added in one portion. A precipitate formed and the resulting mixture was refluxed for 1.5 hours. The mixture was cooled to room temperature and filtered to separate the solids, which were washed with tert-butanol and diethyl ether. The solids were dissolved in water and acidified with 1 N sulfuric acid to form a precipitate. The resulting mixture was extracted with DCM and the combined extracts were washed with brine and water, dried over MgSO$_4$, filtered and concentrated to give a green solid. Recrystallization of this material from methanol provided the title compound (1.15 g, 47%) as an off-white solid, mp 232–233° C.; MS (CI):296 (M+H). Analysis for C$_{13}$H$_{10}$ClNO$_5$: Calc'd: C, 52.81; H, 3.41; N, 4.74; Found: C, 52.75; H, 3.47; N, 4.69.

3-Carbomethoxy-7-chloro-4-hydroxyquinoline-2-carboxylic acid:

To a stirred suspension of dimethyl 7-chloro-4-hydroxyquinoline-2,3-dicarboxylate (1.0 g, 3.38 mmol) in water (20 mL) was added an aqueous solution of sodium hydroxide (0.27 g, 6.75 mmol). Upon addition, the suspension dissolved. The reaction mixture was warmed to 60° C. for 1 hour. After this time the reaction was cooled to room temperature and acidified with concentrated hydrochloric acid. The product was then extracted into diethyl ether and ethyl acetate. The organic extracts were dried over MgSO$_4$, filtered and concentrated in vacuo to provide the title compound as a solid (900 mg). This material was purified by recrystallization employing an ethyl acetate/hexane co-solvent system to provide the title compound (571 mg, 60%) as a white solid mp 296° C. (dec); MS (CI)=238 (M+H). Analysis for C$_{12}$H$_8$NO$_5$Cl.0.45 CH$_3$CO$_2$CH$_2$CH$_3$.0.10 H$_2$O: Calc'd: C, 51.30; H, 3.68; N, 4.34, Found: C, 51.28; H, 3.62; N, 3.97;$^1$H NMR 8.22 (d, J=8.7 Hz, 1H), 7.92 (d, J=1.8 Hz, 1H), 7.28 (dd, J=8.7, 1.8 Hz, 1H), 3.90 (s, 3H).

3-Carbomethoxy-2-pyrrolidinocarbamide-7-chloro-4-hydroxyquinoline:

To a suspension of 3-carbomethoxy-7-chloro-4-hydroxyquinoline-2-carboxylic acid (2.25 g, 8.0 mmol) in THF (20 mL) at ambient temperature under a N$_2$ atmosphere was added DHC (1.65 g, 8.0 mmol) and pyrrolidine (0.596 g, 8.4 mmol). The reaction was stirred room temperature for 15 hours after which time the by-product urea was removed via filtration. The desired product was purified via flash column chromatography employing 5% methanol in chloroform to provide the title compound (2.52 g, 94.3%) as a tan solid, mp=215° C.; MS (CI): 335 (M+H). 300 MHz $^1$H NMR (DMSO-d$_6$): δ 8.12 (d, J=8.7 Hz, 1H), 7.60 (d, 1H, J=1.8 Hz), 7.47 (dd, 1H, J=8.8, 2.0 Hz), 3.69 (s, 3H), 3.40–3.49 (m, 2H), 3.27–3.33 (m, 2H), 1.80–1.96 (m, 4H).

7-Chloro-4-oxo-2-(pyrrolidinylcarbonyl)hydroquinoline-3-carboxylic acid:

To a suspension of 3-carbomethoxy-2-pyrrolidinocarbamide-7-chloro4-hydroxy quinoline (2.52 g, 7.5 mmol) in de-ionized water (40 mL) was added dropwise a solution (20 mL) of an aqueous potassium hydroxide (882 mg, 15.75 mmol). Upon complete addition, the reaction was warmed to 60° C. After 3 hours, the reaction was filtered to remove a small amount of insoluble material. The filtrate was then acidified to pH=1 which yield a white precipitate. The solid was isolated by vacuum filtration, washed with water, and dried at 30° C. in vacuo for 16 hours. This provided the title compound (1.5 g, 64%) as a white solid, mp=225–8° C.; MS (CI): 321 (M+H). 300 MHz $^1$H NMR (DMSO-d$_6$): δ 8.28 (d, J=8.8 Hz, 1H), 7.77 (s, 1H), 7.64 (d, 1H, J=8.7), 3.52–3.57 (m, 2H), 3.17–3.19 (m, 2H), 1.83–1.98 (m, 4H).

(+/−)-N-[(tert-Butoxy)carbonylamino][7-chloro-4-oxo-2-(pyrrolidinylcarbonyl)(3-hydroquinolyl]-N-(cyclopropyl-2-pyridylmethyl)carboxamide.

To a stirred slurry of 7-chloro-4-oxo-2-(pyrrolidinylcarbonyl)hydroquinoline-3-carboxylic acid (1.27 g, 3.99 mmol) in THF (60 mL) was added CMC (1.93 g, 4.56 mmol) and the reaction was stirred for five minutes. To this mixture was added, by dropwise addition, a solution of (+/−)-(tert-butoxy)-N-[(cyclopropyl-2-pyridylmethyl)amino]carboxamide (1.00 g, 3.80 mmol) and DMAP (0.040 g, 0.32 mmol) in THF (20 mL), and the mixture was stirred at room temperature for 1 hour. The mixture was then refluxed overnight. The solution was filtered and the insolubles washed with DCM (2×150 mL). The mother liquor was collected and concentrated to dryness. The resultant solid was subjected to chromatography (SiO$_2$, 95/5 chloroform/methyl alcohol) to give the title compound as a yellow foam (2.08 g, 96%). This material was used as is in the next reaction.

(+/−)-7-Chloro4-hydroxy-2-(1-cyclopropyl-1-pyrid-2-yl)methyl-1,2,5,10-tetrahydropyridazino[4,5-b]quinoline-1,10-dione.

To a stirred solution of (+/−)-N-[(tert-butoxy)carbonylamino][7-chloro-4-oxo-2-(pyrrolidinylcarbonyl)(3-hydroquinolyl]-N-(cyclopropyl-2-pyridylmethyl)carboxamide: (2.08 g, 3.68 mmol) in THF (40 mL) was added methanesulfonic acid (9 mL) and the reaction was stirred overnight. The volatiles were removed in vacuo and to the residual oil was added diethyl ether (80 mL). The mixture was stirred for 10 minutes and then allowed to settle into two layers, an etheral layer and layer of brown oil. The ether was decanted away and the brown oil was dissolved in water (100 mL). This solution was cooled in an ice bath and to this was added sodium chloride (sat. aqueous, 10 mL), followed by solid sodium chloride (5 g). After a short time, a precipitate formed. This precipitate was collected by vacuum filtration and washed with diethyl ether (2×100 mL). The residue was then sonicated in 20 mL of 4/1 diethyl etherimethyl alcohol for fifteen minutes. The material was filtered, washed with diethyl ether and dried in vacuo to give the title compound (0.574 g, 32%) as an off-white powder (m.p.>280° C.). $^1$H NMR (300 MHz, DMSO-d$_6$): δ 0.53 (m, 1H); 0.70 (m, 2H); 0.86 (m, 1H); 1.74 (m, 1H); 5.49 (m, 1H); 7.45 (d, 1H, J=8.7 Hz); 7.71 (m, 1H); 7.97 (m, 2H); 8.09 (m, 1H); 8.28 (m, 1H); 8.73 (m, 1H); 11.97 (br s, 1H); 12.75 (br s, 1H). Calc'd. for C$_{20}$H$_{15}$ClN$_4$O$_3$.1.0NaCl.1.0H$_2$O: C, 50.58; H, 3.69; N, 11.79; Found: C, 50.67; H, 3.71; N, 11.84.

Example 2

(+/−)-7-Chloro-4-hydroxy-2-(1-cyclopropyl-1-pyrid-4-yl)methyl-1,2,5,10-tetrahydropyridazino[4,5-b]quinoline-1,10-dione hydrochloride Cyclopropyl-4-pyridyl ketone.

Dry magnesium powder (0.760 g, 31.2 mmol), which had been previously crushed in a mortar with a pestle, was charged into a dry round bottom flask under a nitrogen atmosphere. To this was added diethyl ether (20 mL), followed by bromocyclopropane (3.77 g, 2.49 mL, 31.2 mmol). A small amount of iodine (0.002 g) was added to initiate formation of the Grignard reagent. The reaction was heated to a gentle reflux for a short period of time (~1 hour) until all of the magnesium metal had reacted. The flask was then cooled in an ice bath and to this was added 4-cyanopyridine (1.62 g, 15.6 mmol). The mixture was stirred for 3 hours, and then carefully quenched with sat. ammonium chloride (3 mL). The reaction was then acidified with 15% aq. hydrochloric acid (3 ML). The mixture was stirred for 20 minutes, and then made basic by the addition of 10 N sodium hydroxide until the pH was approximately 9. To this solution was added ethyl acetate (300 mL), and the aqueous layer was extracted with water (30 mL). The organic layer was washed with brine, dried over $Na_2SO_4$ and evaporated to dryness giving the title compound as a yellow oil (1.0 g, 43%). $^1H$ NMR (300 MHz, DMSO-$d_6$): δ 1.15 (m, 4H); 2.93 (s, 1H); 7.91 (d, 1H; J=6.0 Hz); 8.83 (d, 1H, J=6.0 Hz).

N-1-Aza-2-cyclopropyl-2-(4-pyridyl)vinyl)(tert-butoxy) carboxamide.

To a stirred solution of tert-butylcarbazate (0.95 g, 7.21 mmol) in THF (50 mL) was added cyclopropyl-4-pyridyl ketone (1.06 g, 7.21 mmol), followed by 3 drops of concentrated hydrochloric acid. The reaction was stirred overnight and the solvent removed in vacuo. The resultant solid was chromatographed (SiO$_2$, ethyl acetate as eluant, R$_f$=0.25) to give the title compound as a white solid (0.98 g, 52%). $^1H$ NMR (300 MHz, DMSO-$d_6$): δ 0.40 (m, 2H); 1.07 (m, 2H); 1.49 (s, 9H); 1.76 (m, 1H); 7.60 (d, 2H, J=4.8 Hz); 8.56 (d, 1H, J=4.8Hz).

(+/−)-(tert-Butoxy)-N-[(cyclopropyl-4-pyridylmethyl)amino]carboxamide.

N-1-Aza-2-cyclopropyl-2-(4-pyridyl)vinyl)(tert-butoxy) carboxamide (0.98 g, 3.75 mmol) was dissolved in methyl alcohol (90 mL) and placed in a Parr shaker bottle. To this was added 10% palladium-on-carbon (500 mg) and the reaction was hydrogenated at 40 psi for 18 hours. The catalyst was filtered on diatomaceous earth, washed with methyl alcohol (2×300 mL), and the solvents were removed in vacuo to give an oil. The material was used as is with no further purification (0.77 g, 78%). $^1H$ NMR (300 MHz, DMSO-$d_6$): δ 0.34 (m, 2H); 0.58 (m, 1H); 0.80 (m, 1H); 1.33 (s, 9H); 1.75 (m, 1H); 3.33 (br s, 1H); 4.75 (br s, 1H); 7.38 (d, 2H, J=6.0 Hz); 8.20 (br s, 1H); 8.45 (d, 2H, J=6.0 Hz).

(+/−)-N-[(tert-Butoxy)carbonylamino][7-chloro-4-oxo-2-(pyrrolidinylcarbonyl)(3-hydroquinolyl]-N-(cyclopropyl-4-pyridylmethyl)carboxamide.

To a stirred slurry of 7-chloro-4-oxo-2-(pyrrolidinylcarbonyl)hydroquinoline-3-carboxylic acid, Example 1, (0.99 g, 3.10 mmol) in THF (50 mL) was added CMC (1.48 g, 3.54 mmol) and the reaction was stirred for five minutes. To this mixture was added, via dropwise addition, a solution of (+/−)-(tert-butoxy)-N-[(cyclopropyl-4-pyridylmethyl)amino]carboxamide (0.77 g, 2.95 mmol) and DMAP (0.05 g, 0.40 mmol) in THF (10 mL), and the mixture was stirred at room temperature for 1 hour. The mixture was then refluxed overnight. The solution was filtered hot and the insolubles washed with DCM (2×150 mL). The mother liquor was collected and concentrated to dryness. The resultant solid was subjected to chromatography (SiO$_2$, 95/5 chloroform/methyl alcohol) to give the title compound as a yellow foam. This foam was then triturated with diethyl ether to give the title compound (1.2 g, 68%) as a yellow solid.

(+/−)-7-Chloro-4-hydroxy-2-(1-cyclopropyl-1-pyrid-4-yl)methyl-1,2,5,10-tetrahydropyridazino[4,5-b]quinoline-1,10-dione hydrochloride.

To a stirred solution of (+/−)-N-[(tert-butoxy)carbonylamino][7-chloro-4-oxo-2-(pyrrolidinylcarbonyl)(3-hydroquinolyl]-N-(cyclopropyl-4-pyridylmethyl) carboxamide (1.2 g 2.12 mmol) in THF (40 mL) was added methanesulfonic acid (5 mL) and the reaction was stirred overnight. The volatiles were removed in vacuo and to the residual oil was added diethyl ether (80 mL). The mixture was stirred for 10 minutes and then allowed to settle into two layers, an etheral layer and layer of brown oil. The ether was decanted away and to the brown oil was added water (18 mL). After a short time, a precipitate formed and was discarded. To the remaining filtrate was added solid sodium chloride until the liquid was saturated. This material was left to stand until a precipitate formed. This precipitate was collected by vacuum filtration and washed with diethyl ether (2×100 mL). The solids were then sonicated in water (8 mL), filtered and sonicated in 10 mL of 4/1 diethyl ether/methyl alcohol for fifteen minutes. The material was filtered, washed with diethyl ether and dried in vacuo to give the title compound (0.182 g, 19%) as an off-white powder (m.p>280° C.). $^1H$ NMR (300 MHz, DMSO-$d_6$): δ 0.46 (m, 1H); 0.65 (m, 1H); 0.85 (m, 2H); 1.67 (m, 1H); 5.37 (d, 1H, J=10.2 Hz); 7.45 (dd, 1H, J=2.1, 8.7 Hz); 7.93 (d, 2H, J=5.4 Hz); 8.05 (d, 1H, J=2.1 Hz); 8.14 (d, 2H, J=5.4 Hz); 8.81 (d, 2H, J=5.4 Hz); 12.04 (br s, 1H); 12.75 (br s, 1H). Calc'd. for $C_{20}H_{15}ClN_4O_3 \cdot 1.0HCl \cdot 1.2H_2O$: C, 53.04; H, 4.09; N, 12.37; Found: C, 53.22; H, 4.01; N, 11.93.

Example 3

(+/−)-7-Chloro-4-hydroxy-2-(1-cyclopentyl-1-pyrid-2-yl)methyl-1,2,5,10-tetrahydropyridazino[4,5-b]quinoline-1,10-dione hydrochloride Cyclopentyl-2-pyridyl ketone.

Prepared in an analogous fashion to cyclopropyl-2-pyridyl ketone, Example 1, (45% as an oil). $^1H$ NMR (300 MHz, DMSO-$d_6$): δ 1.66 (m, 6H); 1.84 (m, 2H); 4.17 (m, 1H); 7.66 (m, 1H); 7.98 (m, 2H); 8.74 (d, 1H, J=4.8 Hz).

N-1-Aza-2-cyclopentyl-2-(2-pyridyl)vinyl)(tert-butoxy) carboxamide.

To a stirred solution of tert-butylcarbazate (2.43 g, 13.8 mmol) in THF (50 mL) was added cyclopentyl-2-pyridyl ketone (1.83 g, 13.8 mmol), followed by 3 drops of concentrated hydrochloric acid. The reaction was stirred overnight and the solvent removed ini vacuo. The resultant solid was triturated with hexanes to give the title compound as a white solid (3.35 g, 84%). $^1H$ NMR (300 MHz, DMSO-$d_6$): δ 1.45 (s, 9H); 1.66 (m, 6H); 1.84 (m, 2H); 3.37 (m, 1H); 7.51 (t, 1H, J=4.8, 7.8 Hz); 7.80 (d, 1H, J=8.1 Hz); 8.02 (dd, 1H, J=1.5, 7.8 Hz); 8.74 (d, 1H, J=4.8 Hz).

(+/−)-(tert-Butoxy)-N-[(cyclopentyl-2-2pyridylmethyl) amino]carboxamide.

N-1-Aza-2-cyclopentyl-2-(2-pyridyl)vinyl)(tert-butoxy) carboxamide (2.00 g, 6.9 mmol) was dissolved in methyl alcohol (90 mL) and placed in a Parr shaker bottle. To this was added 10% palladium-on-carbon (800 mg) and the reaction was hydrogenated at 40 psi for 18 hours. The catalyst was filtered on diatomaceous earth, washed with methyl alcohol (2×300 mL), and the solvents were removed in vacuo to give the title compound (1.92 g, 96%) as an oil. $^1$H NMR (300 MHz, DMSO-$d_6$): δ 1.17 (m, 2H); 1.33 (s, 9H); 1.52 (m, 6H); 1.81 (m, 1H); 2.04 (m, 1H); 4.10 (d, 1H, J=4.5 Hz); 4.61 (m, 1H); 7.21 (d, 1H, J=4.8, 7.8 Hz); 7.43 (d, 1H, J=7.8 Hz); 7.73 (dd, 1H, J=1.5, 7.8 Hz); 8.068 (br s, 1H); 8.44 (d, 1H, J=4.8 Hz).

(+/−)-N-[(tert-Butoxy)carbonylamino][7-chloro-4-oxo-2-(pyrrolidinylcarbonyl)(3-hydroquinolyl]-N-(cyclopentyl-2-pyridylmethyl)carboxamide.

To a stirred slurry of 7-chloro-4-oxo-2-(pyrrolidinylcarbonyl)hydroquinoline-3-carboxylic acid, Example 1, (2.21 g, 6.89 mmol) in THF (80 mL) was added CMC (3.34 g, 7.90 mmol) and the reaction was stirred for five minutes. To this mixture was added, by dropwise addition, a solution of (+/−)-(tert-butoxy)-N-[(cyclopentyl-2-pyridylmethyl)amino]carboxamide (1.92 g, 6.59 mmol) and DMAP (0.15 g, 1.22 mmol) in THF (10 mL), and the mixture was stirred at room temperature for 1 hours. The mixture was then refluxed overnight. The solution was filtered hot and the insolubles washed with DCM (2×150 mL). The mother liquor was collected and concentrated to dryness. The resultant solid was subjected to chromatography (SiO$_2$, 95/5 chloroform/methyl alcohol) to give the title compound as a yellow foam. This foam was then triturated with diethyl ether to give the title compound (3.14 g, 80%) as a yellow solid.

(+/−)-7-Chloro-4-hydroxy-2-(1-cyclopentyl-1-pyrid-2-yl)methyl-1,2,5,10-tetrahydropyridazino[4,5-b]quinoline-1,10-dione hydrochloride.

To a stirred solution of (+/−)-N-[(tert-butoxy)carbonyl amino][7-chloro-4-oxo-2-(pyrrolidinylcarbonyl)(3-hydroquinolyl]-N-(cyclopentyl-2-pyridylmethyl) carboxamide (3.14 g, 5.29 mmol) in THF (100 mL) was added methanesulfonic acid (13 mL) and the reaction was stirred overnight. The volatiles were removed in vacuo and to the residual oil was added diethyl ether (200 mL). The mixture was stirred for 10 minutes and then allowed to settle into two layers, an etheral layer and layer of brown oil. The ether was decanted away and to the brown oil was added water (20 mL), followed by sodium chloride (sat. aqueous, 25 mL). After a short time, a precipitate formed and was collected by vacuum filtration. The precipitate was sonicated in water (10 mL), filtered and sonicated in 20 mL of 4/1 diethyl ether/methyl alcohol for fifteen minutes. The material was filtered, washed with diethyl ether and dried in vacuo to give the title compound (0.632 g, 24%) as an off-white powder (m.p>220–225° C.). $^1$H NMR (300 MHz, DMSO-$d_6$): δ 1.27 (m, 2H); 1.55 (m, 3H); 1.70 (m, 3H); 3.02 (m, 1H); 5.95 (d, 1H, J=11.1 Hz); 7.45 (dd, 1H, J=2.1, 8.7 Hz); 7.67 (t, 1H, J=6.0 Hz); 7.84 (d, 1H, J=8.1 Hz); 8.03 (d, 1H, J=2.1 Hz); 8.14 (d, 2H, J=5.4 Hz); 8.21 (t, 1H, J=7.8 Hz); 8.72 (d, 1H, J=4.8 Hz); 12.04 (br s, 1H); 12.70 (br s, 1H). Calc'd. for $C_{22}H_{19}ClN_4O_3 \cdot 1.0$ HCl$\cdot 1.5H_2O$: C, 54.33; H, 4.76; N, 11.51; Found: C, 54.03; H, 4.40; N, 11.39.

Example 4

(+/−)-7-Chloro-4-hydroxy-2-(1-phenyl-1-pyrid-4-yl) methyl-1,2,5,10-tetrahydropyridazino[4,5-b] quinoline-1,10-dione N-1-Aza-2-Phenyl-2-(4-pyridyl)vinyl)(tert-butoxy) carboxamide.

A solution of 4-benzoylpyridine (5.0 g, 27.3 mmoles), tert-butylcarbazate (3.61 g, 27.3 mmoles), and 3 drops of concentrated hydrochloric acid in THF was stirred at room temperature for 18 hours. The reaction was concentrated under reduced pressure to give a yellow oil. The oil was purified by trituration with ether/hexane (1/1) to obtain the title compound as a white solid (5.43 g, 67% yield). $^1$H NMR (300 MHz, DMSO-$d_6$): δ 1.44 (s, 9H), 7.32 (m, 3H); 7.38 (m, 3H, ); 7.58 (m, 1H;8.57 (d, 1H, J=1.5 Hz ); 8.74 (d, 1H, J=1.5 Hz); 9.15 (s, 1H); 9.48 (s, 1H).

(+/−)-(tert-Butoxy)-N-[(phenyl-4-pyridylmethyl)amino] carboxamide.

A mixture of 10% palladium on carbon (0.55 g) and N-1-aza-2-phenyl-2-(4-pyridyl)vinyl)(tert-butoxy) carboxamide (2.06 g, 6.93 mmol) in methanol (200 mL). was hydrogenated (50 psi) at room temperature for 18 hour. The reaction was filtered through diatomaceous earth and the filtrate evaporated under reduced pressure to give the title compound as a gold oil (2.08 g, quantitative recovery). $^1$H NMR (300 MHz, DMSO-$d_6$): δ 1.36 (s, 9H); 5.10 (s, 1H); 5.27 (s, 1H, ); 7.31 (m, 3H); 7.42 (m, 4H); 8.36 (s, 1H); 8.75 (d, 2H, J=4 Hz).

(+/−)-N-[(tert-butoxy)carbonylamino][7-chloro-4-oxo-2-(pyrrolidinylcarbonyl)(3-hydroquinolyl)]-N-(phenyl-4-pyridylmethyl)carboxamide.

A mixture of 7-chloro-4-oxo-2-(pyrrolidinylcarbonyl) hydroquinoline-3-carboxylic acid, Example 1, (3.60 g, 11.2 mmol), (+/−)-(tert-butoxy)-N-[(phenyl-4-pyridylmethyl) amino]carboxamide (3.37 g, 11.2 mmol), and cyclohexyl-3-(2-morpholinoethyl)carbodiimide metho-p-toluenesulfonate (7.20 g, 17.0 mmol) in THF (350 mL, dry) was refluxed for 18 hours. The reaction was filtered and the filtrate concentrated under reduced pressure. The residue was taken up in DCM (300 mL), washed with water (2×200 mL), and dried over MgSO$_4$. Concentration of the organic layer in vacuo provided a gold oil. The title compound was purified by silica gel column chromatography using methanol/chloroform (5/95) as eluant. The title compound was obtain as an tan solid (3.97 g, 59%). This material was used in the following reaction. MS (+CI) m/z 600/602.

(+/−)-7-Chloro-4-hydroxy-2-(1-phenyl-1-pyrid-4-yl) methyl-1,2,5,10-tetrahydropyridazino[4,5-b]quinoline-1, 10-dione.

A solution of N-[(tert-butoxy)carbonylamino][7-chloro-4-oxo-2-(pyrrolidinylcarbonyl)(3-hydroquinolyl)]-N-(phenyl-4-pyridylmethyl)carboxamide (3.94 g, 6.54 mmol), methanesulfonic acid (5 mL, 7.41 g, 77 mmol), and THF (100 mL) were stirred at room temperature for 48 hours. The reaction was concentrated in vacuo to a gold oil. The oil was taken up in water and filtered to remove insolubles. The filtrate was neutralized with sodium hydroxide (5 N aqueous, pH=7), and the resulting solid filtered and sonicated in methyl alcohol/diethyl ether (1/1, 20 ml). The mixture was filtered and the collected solids dried to give the title compound (0.30 g, 6.0% yield). $^1$H NMR (300 MHz, DMSO-$d_6$): δ 2.32 (s, 3H, methanesulfonic acid), 7.17 (d, 2H, J=6 Hz); 7.40 (m, 8H); 8.07 (d, 1H, J=4.2 Hz); 8.17 (d, 1H, J=8.7 Hz); 8.48 (d, 2H, J=6 Hz); 12.73(br s, 1H). Calc'd. for $C_{23}H_{15}ClN_4O_3 \cdot 3.0CH_3SO_3Na \cdot 0.25H_2O$: C, 39.13; H, 3.16; N, 6.96. Found: C, 39.29; H, 3.18; N, 7.00.

Example 5

(+/−)-7-Chloro-4-hydroxy-2-(1-(3-methylpyrid-4-yl))ethyl-1,2,5,10-tetrahydropyridazino[4,5-b]quinoline-1,10-dione 4-Cyano-3-methylpyridine.

To a cooled (0° C.) round bottom flask charged with 3-picoline-N-oxide (4.53 g, 42 mmol) was added dimethylsulfate (5.8 g, 47 mmol). The mixture was stirred for 18 hours and allowed to warm to room temperature. To this mixture was added potassium cyanide (3.25 g, 50 mmol) dissolved in ethyl alcohol/water (75 mL, 1:1). The reaction was stirred at room temperature for 18 hours, concentrated to half the volume and diluted with chloroform (100 mL). The organic layer was separated and washed with sodium chloride (sat. 25 mL) and dried over $Na_2SO_4$. The solvent was removed and the residual material was chromatographed ($SiO_2$, hexanes/ethyl acetate) to give the title compound as off-white crystals (2.01 g, 41%). $^1$H NMR (300 MHz, DMSO-$d_6$): δ 2.55 (s, 3H); 7.47 (d, 1H); J=5.1 Hz); 8.60 (d, 1H, J=5.1 Hz); 8.68 (s, 1H).

The intermediate pyridylketone was made using commercially available methylmagnesium bromide (1.4 M in toluene/THF) and the nitrile described above using the method previously described in Example 1. Conversion to (+/−)-7-chloro-4-hydroxy-2-(1-methylpyridy-4-yl)methyl)-1,2,5,10-tetrahydropyridazino[4,5-b]quinoline-1,10-dione was likewise accomplished in a manner analogous to Example 1 to give an off-white powder. $^1$H NMR (300 MHz, DMSO): δ 1.65 (d, 3H, J=6.9 Hz); 2.34 (s, 3H, $CH_3SO_3H$); 2.53 (s, 3H); 6.14 (q, 1H, J=6.9 Hz); 7.42 (dd, 1H, J=1.8, 8.7 Hz); 7.87 (d, 1H, J=6.3 Hz); 8.04 (d, 1H, J=1.8 Hz); 8.13 (d, 1H, J=8.7 Hz); 8.73 (d, 1H, J=6.3 Hz); 8.80 (s, 1H); 12.02 (br s, 1H); 12.73 (br s, 1H).

Example 6

(+/−)-7-Chloro-4-hydroxy-2-(1-methyl(6-methylpyrid-2-yl)methyl)-1,2,5,10-tetrahydropyridazino[4,5-b]quinoline-1,10-dione methanesulfonate 2-Cyano-6-methylpyridine.

2-Cyano-6-methyypyridine was made using 2-picoline-N-oxide as the starting material in a manner analogous to the procedure described in Example 5: $^1$H NMR (300 MHz, DMSO-$d_6$): δ 2.61 (s, 3H); 7.38 (d, 1H, J=7.8 Hz): 7.49 (d, 1H, J=7.8 Hz); 7.72 (t, 1H, J=7.8 Hz).

The title compound, an off-white powder, was prepared in a manner analogous to Example 5. $^1$H NMR (300 MHz, DMSO-$d_6$-TFA shake): δ 1.78 (d, 3H, J=6.9 Hz); 2.79 (s, 3H); 6.44 (q, 1H, J=6.9 Hz); 7.42 (dd, 1H, J=2.1, 8.7 Hz); 7.78 (s, 1H); 7.96 (m, 3H); 8.56 (t, 1H, J=8.1 Hz). Calc'd. for $C_{19}H_{15}ClN_4O_3 \cdot 1.1\ CH_3SO_3H \cdot 0.45\ H_2O$: C, 48.61; H, 4.12; N, 11.28; Found: C, 48.72; H, 4.18; N, 11.19.

In the conversion of 2-picoline-N-oxide to 2-cyano-6-methylpyridine, the reaction gave rise to a side-product, 4-cyano-2-methylpyridine, which was separated from the title compound by column chromatography ($SiO_2$, hexane/ethyl acetate 90:10 to 80:20 gradient). 4-cyano-2-methylpyridine: $^1$H NMR (300 MHz, DMSO-$d_6$): δ 2.64 (s, 3H); 7.34 (d, 1H, J=5.1 Hz); 7.40 (s, 1H); 8.68 (d, 1H, J=5.1 Hz). This material was used in Example 8, below.

Example 7

(+/−)-7-Chloro-4-hydroxy-2-(1-methyl(3-methylpyrid-2-yl)methyl)-1,2,5,10-tetrahydropydridazino[4,5-b]quinoline-1,10-dione methanesulfonate The title compound was made in a manner analogous to the procedure described in Example 5, using 2-cyano-3-methylpyridine and methylmagnesium bromide (1.4 M in toluene/THF) as starting materials to give the title compound as an off-white powder. $^1$H NMR (300 MHz, DMSO-$d_6$-tfa shake): δ 1.82 (d, 3H, J=6.9 Hz); 2.48 (s, 3H); 6.21 (q, 1H, J=6.9 Hz); 7.45 (dd, 1H, J=1.8, 8.7 Hz); 7.96 (dd, 1H, J=5.7, 7.5 Hz); 8.06 (d, 1H, J=1.8 Hz); 8.16 (d, 1H, J=8.7 Hz); 8.48 (d, 1H, J=7.5 Hz); 8.73 (d, 1H, J=4.8 Hz). Calc'd. for $C_{19}H_{15}ClN_4O_3 \cdot 4\ CH_3SO_3H \cdot 0.2H_2O$: C, 35.84; H, 4.11; N, 7.27; Found: C, 35.47; H, 3.73; N, 7.36.

Example 8

(+/−)-7-Chloro-4-hydroxy-2-(1-methyl(2-methylpyrid-4-yl)methyl)-1,2,5,10-tetrahydropyridazino[4,5-b]quinoline-1,10-dione methanesulfonate The title compound was made by analogy to the procedure described in Example 1, using 4-cyano-2-methylpyridine (described in Example 6) and methylmagnesium bromide (1.4 M in toluene/THF) as starting materials to give the title compound as an off-white powder. $^1$H NMR (300 MHz, DMSO-$d_6$): δ 1.72 (d, 3H, J=6.9 Hz); 2.32 (s, 3H, $CH_3SO_3H$); 2.67 (s, 3H); 6.21 (q, 1H, J=6.9 Hz); 7.45 (dd, 1H, J=1.8, 8.7 Hz); 7.76 (d, 1H, J=6.0 Hz); 7.79 (s, 1H); 8.06 (d, 1H, J=1.8 Hz); 8.15 (d, 1H, J=8.7 Hz); 8.66 (d, 1H, J=6.0 Hz); 12.04 (br s, 1H); 12.70 (br s, 1H). Calc'd. for $C_{19}H_{15}ClN_{4O3} \cdot 1.35CH_3SO_3H \cdot 1.05H_2O$: C, 45.99; H, 4.27; N, 10.54; Found: C, 46.00; H. 4.21; N, 10.60.

Example 9

(+/−)-7-Chloro-4-hydroxy-2-(1-methyl(3-trifluoromethylpyrid-2-yl)methyl)-1,2,5,10-tetrahydropyridazino[4,5-b]quinoline-1,10-dione 2-Cyano-3-trifluromethylpyridine To a stirred solution of 2-chloro-3-trifluoromethylpyridine (5.00 g, 27.5 mmol) in DMSO (20 mL) was added potassium cyanide (2.15 g, 33.0 mmol) and the mixture heated to 100° C. for 18 hours. The mixture was diluted with ethyl acetate and extracted with water (80 mL). The organic layer was separated and evaporated to give a brown residue. The material was chromatographed ($SiO_2$, hexanes/ethyl acetate gradient 85/15 to 80/20) to give the intermediate nitrile as an oil (0.8 g, 17%). $^1$H NMR (300 MHz, DMSO-$d_6$): δ 7.73 (dd, 1H, J=8.1, 4.5 Hz); 8.15 (d, 1H, J=8.1 Hz); 8.92 (d, 1H, J=4.5 Hz).

The intermediate pyridylketone was made using commercially available methyl magnesium bromide (1.4 M in toluene/THF) and the nitrile described above using the method previously described in Example 5. Conversion to (+/−)-7-chloro-4-hydroxy-2-(1-methyl(3-trifluromethylpyridy-2-yl)methyl)-1,2,5,10-tetrahydropyridazino[4,5-b]quinoline-1,10-dione was likewise accomplished by a process analogous to that in Example 5 to give an off white powder. $^1$H NMR (300 MHz, DMSO-$d_6$): δ 1.67 (d, 3H, J=6.6 Hz); 6.181 (q, 1H, J=6.6 Hz); 7.42 (d, 1H, J=8.7 Hz); 7.53 (dd, 1H, J=5.1, 7.8 Hz); 8.03 (d, 1H, J=2.1 Hz); 8.14 (d, 1H, J=8.7 Hz); 8.16 (d, 1H, J=7.8 Hz); 8.76 (d, 1H, J=4.5 Hz); 11.92 (br s, 1H); 12.40 (br s, 1H).

Example 10

(+/−)-7-Chloro-4-hydroxy-2-(1-pyrid-2-yl-N-oxide) ethyl-1,2,5,10-tetrahydropyridazino[4,5-b]quinoline-1,10-dione N-(1-Aza-2-(2-pyridyl)prop)-1-enyl)(tert-butoxy) carboxarride.

To a stirred solution of tert-butylcarbazate (2.18 g, 16.5 mmol) in THF (40 mL) was added 2-acetylpyridine (2.00 g, 16.5 mmol), followed by 3 drops of concentrated hydrochloric acid. After 1 h, the reaction turned cloudy, and the solvent was removed in vacuo. The resultant solid was triturated with hexanes and filtered to give the title compound as a white solid (3.12 g, 80%). $^1$H NMR (300 MHz, DMSO-$d_6$): δ 1.49 (s, 9H); 7.38 (dd, 1H, J=4.8, 6.7 Hz); 7.94 (m, 1H); 7.99 (d, 1H, J=7.5 Hz); 8.58 (d, 1H, J=4.2 Hz); 10.04 (s, 1H).

(+/−)-(tert-Butoxy)-N-[(2-pyridylethyl)amino] carboxamide.

N-(1-Aza-2-(2-pyridyl)prop-1-enyl)(tert-butoxy) carboxamide (2.0 g, 8.5 mmol) was dissolved in methyl alcohol (80 mL) and placed in a Parr shaker bottle. To this was added 10% palladium-on-carbon (850 mg) and the reaction was hydrogenated at 40 psi for 24 h. The mixture was filtered through diatomaceous earth, which was washed with methyl alcohol (3×100 mL). The combined filtrate and washes were concentrated in vacuo. The resultant oil (ca. 1.8 g) was used in the following reaction without further purification. $^1$H NMR (300 MHz, DMSO-$d_6$): δ 1.19 (d, 3H, J=6.6 Hz); 1.33 (s, 9H); 4.11 (m, 1H); 4.79 (m, 1H); 7.22 (m, 1H); 7.49 (d, 1H, J=7.8 Hz); 8.22 (m, 1H, J=1.5, 2.4 Hz); 8.49 (d, 1H, J=4.2 Hz).

(+/−)-N-[(tert-Butoxy)carbonylamino][7-chloro-4-oxo-2-(pyrrolidinylcarbonyl)(3-hydroquinolyl)-N-(2-pyridylethyl) carboxamide.

To a stirred slurry of 7-chloro-4-oxo-2-(pyrrolidinylcarbonyl)hydroquinoline-3-carboxylic acid, Example 1, (2.43 g, 7.57 mmol) in THF (100 mL) was added CMC (3.69 g, 8.72 mmol) and the reaction was stirred for five minutes. To this mixture was added dropwise a solution of (+/−)-(tert-butoxy)-N-[(2-pyridylethyl)amino] carboxamide (1.8 g, 7.59 mmol) and DMAP (0.160 g, 1.30 mmol) in THF (20 mL). The mixture was stirred at room temperature for 45 minutes and then refluxed overnight. The cooled solution was filtered and the collected insolubles washed with DCM (2×150 mL). The combined filtrate and washes were concentrated in vacuo to dryness. The resultant yellow foam was subjected to chromatography (silica gel, 95/5 chloroform/methyl alcohol) to give the title compound as a yellow foam (3.3 g, 81%).

(+/−)-7-Chloro-4-hydroxy-2-(1-pyrid-2-yl)ethyl-1,2,5, 10-tetrahydropyridazino[4,5-b]quinoline-1,10-dione methanesulfonate.

To a stirred solution of (+/−)-N-[(tert-butoxy) carbonylamino][7-chloro-4-oxo-2-(pyrrolidinylcarbonyl)(3-hydroquinolyl]-N-(2-pyridylethyl)carboxamide (3.0 g, 5.56 mmol) in THF (100 mL) was added methanesulfonic acid (15 mL) and the reaction was stirred overnight. The volatiles were removed in vacuo and the resultant oil was poured on to crushed ice. A fine precipitate formed which was filtered to give an orange solid. This material was washed with diethyl ether, and then sonicated in 20 mL of 1/1 diethyl ether/methyl alcohol for fifteen minutes and filtered. The collected solids were sonicated again in 85 mL of the same solvent system for an additional fifteen minutes. The insoluble materials were collected, washed with the same solvent system and dried at 55° C. for 12 h to give the title compound (1.29 g, 48%) as an off-white powder (m.p.>290° C). $^1$H NMR (300 MHz, DMSO-$d_6$): δ 1.77 (d, 3H, J=6.9 Hz); 2.34 (s, 3H, $CH_3SO_3H$); 6.38 (q, 1H, J=6.9 Hz); 7.44 (dd, 1H, J=1.5, 8.7 Hz); 7.82 (m, 2H); 7.90 (d, 1H, J=8.1 Hz); 8.04 (d, 1H, J=8.7 Hz); 8.38 (app t, 1H, J=7.5 Hz); 8.82 (d, 1H, J=5.1 Hz); 11.98 (s, 1H); 12.80 (s, 1H). Calc'd. for $C_{18}H_{13}ClN_4O_3 \cdot CH_3SO_3H \cdot H_2O$: C, 47.25; H, 3.96; N, 11.60. Found: C, 47.26; H, 3.67; N, 11.50.

(+/−)-7-Chloro-4-hydroxy-2-(1-pyrid-2-yl-N-oxide) ethyl-1,2,5,10-tetrahydropyridazino[4,5-b]quinoline-1,10-dione.

To a stirred suspension of (+/−)-7-chloro-4-hydroxy-2-(1-pyrid-2-yl)ethyl-1,2,5,10-tetrahydropyridazino[4,5-b]quinoline-1,10-dione methanesulfonate (0.420 g, 0.86 mmol) in methyl alcohol (1.0 mL) was added choline hydroxide (0.49 mL, 45% in MeOH, 1.73 mmol) and the solution stirred until all had dissolved. To this was added 3-chloroperoxybenzoic acid (0.316 g, 57–86% purity, 1.04 mmol -1.57 mmol) and the solution stirred 24 hours. An additional portion of 3-chloroperoxybenzoic acid (0.08 g, 57–86% purity, 0.2 mmol-0.3 mmol) was added and the reaction stirred 2 days. The solid was then filtered, washed with methyl alcohol. The material was triturated in diethyl ether, filtered and dried in vacuo (200 mtorr, 60° C., 2 hours) to give the title compound (0.157 g, 47%) as a yellow solid. $^1$H NMR (300 MHz, DMSO-$d_6$): δ 1.65 (d, 3H, J=6.9 Hz) 6.35 (d, 1H, J=6.9 Hz); 7.32 (m, 3H); 7.42 (d, 1H, J=8.7 Hz); 8.03 (s, 1H); 8.14 (d, 1H, J=8.7 Hz); 8.24 (d, 1H, J=5.7 Hz); 11.91 (br s, 1H); 12.50 (br s, 1H). MS (+Cl) m/z 385/387.

Example 11

(+/−)-7-Chloro-4-hydroxy-2-(1-pyrid-4-yl-N-oxide) ethyl-1,2,5,10-tetrahydrpyridazino[4,5-b]quinoline-1,10-dione N-(1-aza-2-(4-pyridyl)prop-1-enyl)(tert-butoxy) carboxamide.

To a stirred solution of tert-butylcarbazate (2.18 g, 16.5 mmol) in THF (40 mL) was added 4-acetylpyridine (2.00 g, 16.5 mmol), followed by 3 drops of concentrated hydrochloric acid. After 1 h, the reaction turned cloudy, and the solvent was removed in vacuo. The resultant solid was triturated with hexanes and filtered to give the title compound as a white solid (3.88 g, 100%). $^1$H NMR (300 MHz, DMSO-$d_6$): δ 1.47 (s, 9H); 7.55 (dd, 2H, J=1.5, 4.5 Hz); 7.97 (s, 1H); 7.99 (d, 2H, J=4.5 Hz); 11.22 (s, 1H).

(+/−)-(tert-Butoxy)-N-[(4-pyridylethyl)amino] carboxamide.

N-(1-Aza-2-(4-pyridyl)prop-1-enyl)(tert-butoxy) carboxamide (2.0 g, 8.51 mmol) was dissolved in ethyl alcohol (90 mL) and placed in a Parr shaker bottle. To this was added 10% palladium-on-carbon (500 mg) and the reaction was hydrogenated at 40 psi for 24 h. The mixture was filtered through diatomaceous earth, which was washed with methyl alcohol (3×100 mL). The combined filtrate and washes were concentrated in vacuo. The resultant material was triturated with 90/10 hexanes/DCM to give the title compound as a white solid (1.34 g, 66%). $^1$H NMR (300 MHz, DMSO-$d_6$): δ 1.19 (d, 3H, J=6.6 Hz); 1.34 (s, 9H); 4.09 (m, 1H); 4.86 (m, 1H); 7.35 (d, 2H, J=5.7 Hz); 8.21 (s, 1H); 8.47 (d, 2H, J=5.7 Hz).

(+/−)-N-[(tert-Butoxy)carbonylamino][7-chloro-4-oxo-2-(pyrrolidinylcarbonyl)(3-hydroquinolyl]-N-(4-pyridylethyl) carboxamide.

To a stirred slurry of 7-chloro-4-oxo-2-(pyrrolidinylcarbonyl)hydroquinoline-3-carboxylic acid, Example 1, (1.66 g, 5.17 mmol) in THF (40 mL) was added CMC (2.82 g, 6.72 mmol) and the reaction was stirred for five minutes. To this mixture was added dropwise a solution of (+/−)-(tert-butoxy)-N-[(4-pyridylethyl)amino] carboxamide (1.3 g, 5.69 mmol) and DMAP (0.080 g, 0.65 mmol) in THF (20 mL). After stirring the reaction mixture at room temperature for 2 hours, an additional portion of CMC (0.500 g) was added and the mixture was refluxed overnight. The solution was cooled to 50° C., another portion of diimide added (0.500 g) and the mixture was refluxed for 3 h. The cooled reaction mixture was filtered and the collected insolubles washed with DCM (2×150 mL). The combined filtrate and washes were concentrated in vacuo to dryness. The resultant yellow foam was subjected to chromatography (silica gel, 92/8 chloroform/methyl alcohol) to give the title compound as a yellow foam (2.04 g, 73%).

(+/−)-7-Chloro-4-hydroxy-2-(1-pyrid-4-yl)ethyl-1,2,5,10-tetrahydropyridazino[4,5-b]quinoline-1,10-dione methanesulfonate.

To a stirred solution of (+/−)-N-[(tert-butoxy)carbonyl amino][7-chloro-4-oxo-2-(pyrrolidinylcarbonyl)(3-hydroquinolyl]-N-(4-pyridylethyl)carboxamide (2.04 g, 3.8 mmol) in THF (100 mL) was added methanesulfonic acid (13.5 mL) and the reaction was stirred overnight. The volatiles were removed in vacuo and the resultant oil was poured on to crushed ice. A fine precipitate formed which was filtered to give an orange solid. This material was washed with diethyl ether, and then sonicated in 40 mL of 1/1 diethyl ether/methyl alcohol for fifteen minutes. The material was washed with diethyl ether to give the title compound (0.715 g, 40%) as an off-white powder (m.p. 245–248° C.). $^1$H NMR (300 MHz, DMSO-d$_6$): δ 1.74 (d, 3H, J=6.9 Hz); 2.31 (s, 3H, C$\underline{H}_3$SO$_3$H); 6.24 (q, 1H, J=6.9 Hz); 7.45 (dd, 1H, J=1.8, 8.7 Hz); 7.86 (m, 2H); 8.05 (d, 1H, J=1.8 Hz); 8.14 (d, 1H, J=8.7 Hz); 8.82 (m, 2H); 12.03 (s, 1H); 12.71 (s, 1H). Calc'd. for C$_{18}$H$_{13}$ClN$_4$O$_3$.CH$_3$SO$_3$H.0.8 H$_2$O: C, 47.61; H, 3.91; N, 11.68. Found: C, 47.84; H, 3.79; N, 11.54.

(+/−)-7-Chloro-4-hydroxy-2-(1-pyrid-4-yl-N-oxide) ethyl-1,2,5,10-tetrahydropyridazino[4,5-b]quinoline-1,10-dione.

To a stirred suspension of (+/−)-7-chloro-4-hydroxy-2-(1-pyrid-4-yl)ethyl-1,2,5,10-tetrahydropyridazino[4,5-b]quinoline-1,10-dione methanesulfonate (0.400 g, 0.8 mmol) in methyl alcohol (1.5 mL) was added choline hydroxide (0.49 mL, 45% in MeOH, 1.73 mmol) and the solution stirred until all had dissolved. To this was added 3-chloroperoxybenzoic acid (0.316 g, 57–86% purity, 1.04 mmol–1.57 mmol) and the solution stirred 3 hours. The solid was then filtered, washed with methyl alcohol and dried in vacuo (200 mtorr) to give the title compound (0.176 g, 57%) as a yellow solid. $^1$H NMR (300 MHz, DMSO-d$_6$): δ 1.65 (d, 3H, J=6.9 Hz) 6.14 (d, 1H, J=6.9 Hz); 7.30 (d, 2H, J=6.6 Hz); 7.42 (d, 1H, J=8.7 Hz); 8.03 (s, 1H); 8.14 (m, 3H); 11.92 (br s, 1H); 12.61 (br s, 1H). MS (+CI) m/z 385/387.

Tests for Biological Function:

Test A: Inhibition of Binding of [$^3$H]-MDL105,519:

Binding of compounds to the NMDA receptor glycine site may be assessed by measuring the ability of test compounds to inhibit the binding of tritiated MDL105,519 to brain membranes bearing the receptor.

Rat Brain Membranes: The rat brain membranes used in the experiments were obtained from Analytical Biological Services Inc., and were prepared substantially in accordance with the method of B. M. Baron et al., *J. Pharmacol. Exp. Ther.* 250, 162 (1989). Briefly, fresh brain tissue including cerebral cortex and hippocampus from male Sprague Dawley rats was homogenized in 0.32 M sucrose and centrifuged at low speed to separate cellular membranes from other cellular components. The membranes were then washed 3 times using deionized water, followed by treatment with 0.04% Triton X-100. Finally, membranes were washed six times in 50 mM Tris citrate buffer, pH 7.4, and frozen at −80° C. until use.

[$^3$H]MDL105,519 (72 Ci/mmol) was purchased from Amersham. Cold MDL105,519 was purchased from Sigma/RBI. Binding assays were performed substantially in accordance with the protocol of B. M. Baron et al., *J. Pharmacol. Exp. Ther.* 279, 62 (1996), as follows. On the day of the experiment, brain membranes were thawed at room temperature and suspended in 50 mM tris acetate buffer, pH 7.4 ("TAB"). Seventy-five micro grams per milliliter protein (by using the BioRad dye) were used for competition binding. The experiments were carried out using 96-well plates. Membranes were incubated with 20 μL of compounds of various concentrations and 1.2 nM [$^3$H]ML105,519 for 30 minutes at room temperature in a total volume of 250 μL. Non specific binding was determined by using 100 μM of unlabeled MDL105,519. The unlabeled MDL105,519 and compounds were dissolved as 12.5 mM stock solutions in DMSO. Final DMSO concentration in each well was kept below 1%, which concentration was found not to alter the binding results. After incubation, unbound [$^3$H]ML105,519 was removed by filtration onto GF/B Unifilter plates using a Packard harvester. Filters were washed four times with ice cold TAB (total of 1.2 mL buffer). The plates were dried overnight at room temperature and bound radioactivity was measured on a Packard TopCount after the addition of 45 μL per well of the MICROSCINT O.

Human Brain Membranes: Human brain membranes were obtained from Analytical Biological Services Inc., and assays were performed as described for rat membranes.

Data analysis: Data was analyzed using a Microsoft Excel spreadsheet and GraphPad Prizm software and potency of compounds is expressed as the Ki (nM).

Test B: Formalin Test:

The Formalin test is an assay that assesses the capacity of a compound to inhibit formalin-induced nociceptive behaviors in rats (D. Dubuisson, et al., *Pain* 4, 161–174 (1977); H. Wheeler-Aceto et al., *Psyclopharmacology* 104, 35–44 (1991); T. J. Coderre, et al., *Pain* 54, 43–50 (1993)). In the test, two distinctive phases of formalin-induced behaviors are observed. A first phase response, caused by acute nociception to the noxious chemical (formalin) injected into the paw, occurs between zero and five minutes. A quiescent period of 5 to 15 min post injection follows. After the quiescent period a second phase response, caused by sensitization of the central neurons in the dorsal horn, occurs after 15 minutes and lasts up to 60 minutes. Sensitization of the central neurons in the spine augments a noxious afferent input and causes a stronger pain barrage to be transmitted to the brain. Therefore, inhibition of the second phase response indicates a central mechanism of drug action.

The procedure for the formalin test may be performed as follows: male rats are placed in a plexiglass chamber and observed for 30–45 min. to observe their baseline activity. Animals would either be pretreated with vehicle or with different doses of a test compound and are dosed with vehicle or test compound three hours prior to injection of 0.05 mL of sterile 1% formalin under the dorsal skin of a hind paw. The number of paw flinches (responses) during the first phase (0–5 min.) and the second phase (20–35 min.) are scored and recorded. Flinch response can be compared with the mean score of a saline control group and calculated as percentage inhibition. The $ED_{50}$ is the dose of compound which produced 50% inhibition of nociceptive response in the first or second phase response.

% inhibition of nociceptive response can be calculated as:

100×(number of responses in vehicle group−number of responses in compound group)/(number of responses in compound group)

Student's t-test can be used for statistical analysis to determine the significance of compound effects.

Test C: Neuropathic Pain Model (Chronic Constriction Injury):

The anti-hyperalgesic properties of a compound may be tested with the Chronic Constriction Injury ("CCI") model. The test is a model for neuropathic pain associated with nerve injuries that can arise directly from trauma and compression, or indirectly from a wide range of diseases such as infection, cancer, metabolic conditions, toxins, nutritional deficiencies, immunological dysfunction, and musculoskeletal changes. In the model a unilateral peripheral hyperalgesia is produced in rats by nerve ligation (G. J. Bennett, et al., *Pain* 33, 87–107 (1988)).

Procedurally, Sprague-Dawley rats (250–350 g) are anesthetized with sodium pentobarbital and the common sciatic nerve exposed at the level of the mid thigh by blunt dissection through the biceps femoris. A section of nerve (about 7 mm), proximal to the sciatic trifucation, is freed of tissue and ligated at four positions with chromic gut suture, with the suture tied with about 1 mm spacing between ligatures. The incision is closed in layers and the animals allowed to recuperate. Thermal hyperalgesia is measured using a paw-withdrawal test (K. Hargreaves, et al., *Pain* 32, 77–88 (1988)). To perform the test, animals are habituated on an elevated glass floor and a radiant heat source aimed at the mid-plantar hindpaw (sciatic nerve territory) through the glass floor with a 20 second cut-off to prevent injury to the skin. The latencies for the withdrawal reflex in both hind paws are recorded.

In this test, paws with ligated nerves show shorter paw withdrawal latencies compared to the unoperated or sham operated paws. Responses to test compounds are evaluated at different times after oral administration to determine the onset and duration of compound effect. When performing the test, groups of CCI rats would receive either vehicle or the test compound orally three times daily for 5 days. Paw withdrawal latencies can be measured each day 10 min. before and two or three hr. after the first daily dose. Compound efficacy is calculated as mean percentage decrease of hyperalgesia compared to a vehicle-treated group. Compound potencies may be expressed as the minimum effective dose (MED) in mg/Kg/day that yields a % decrease in hyperalgesia that is statistically significant, where the % anti-hyperalgesic effect may be calculated as follows:

(Mean of vehicle group−Mean of compound group)×100/(Mean of vehicle group)

Data analysis can be performed by the multiple means comparison (Dunnett's test).

Table 1 shows the results from Test A for certain compounds of the invention.

TABLE 1

|  | Test A Ki (nM) |
| --- | --- |
| Ex. 1 | 996 |
| Ex. 2 | 751 |
| Ex. 3 | >10 µM |
| Ex. 4 | 3690 |
| Ex. 5 | 907 |
| Ex. 7 | 1780 |
| Ex. 8 | 228 |
| Ex. 10 | 2570 |
| Ex. 11 | 2420 |

What is claimed is:

1. A compound according to structural diagram I;

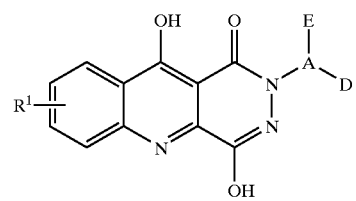

wherein:

$R^1$ is halo;

A is CH;

E is selected from phenyl and $C_{3-7}$cycloalkyl;

D is selected from pyridyl and N-oxide of pyridyl, or tautomers or pharmaceutically-acceptable salts thereof.

2. A compound according to claim 1, wherein:

E is selected from phenyl and $C_{3-5}$cycloalkyl.

3. A compound of claim 1, according to structural diagram II:

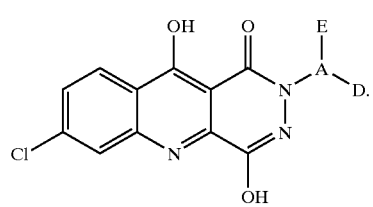

4. A compound according to claim 3, wherein:

E is selected from phenyl and $C_{3-5}$cycloalkyl.

5. A compound according to claim 1, selected from:

7-chloro-4-hydroxy-2-(1-(1-cyclopropyl-1-pyrid-2-ylmethyl)-1,2,5,10-tetrahydropyridazino[4,5-b]quinoline-1,10-dione;

7-chloro-4-hydroxy-2-(1-cyclopropyl-1-pyrid-4-ylmethyl)-1,2,5,10-tetrahydropyridazino[4,5-b]quinoline-1,10-dione;

7-chloro-4-hydroxy-2-(1-cyclopentyl-1-pyrid-2-ylmethyl)-1,2,5,10-tetrahydropyridazino[4,5-b]quinoline-1,10-dione, and 7-chloro-4-hydroxy-2-(1-phenyl-1-pyrid-4-ylmethyl)-1,2,5,10-tetrahydropyridazino[4,5-b]quinoline-1,10-dione.

6. A method for treating a subject suffering from pain comprising administering a pain-ameliorating effective amount of a compound according to structural diagram I,

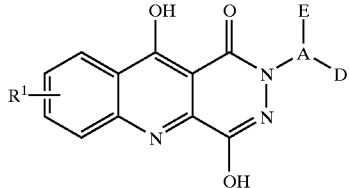

wherein:
 $R^1$ is halo;
 A is CH;
 E is selected from phenyl and $C_{3-7}$cycloalkyl;
 D is selected from pyridyl and N-oxide of pyridyl,
or tautomers or pharmaceutically-acceptable salts thereof.

7. A method according to claim 6, wherein in a compound according to structural diagram I:
 E is selected from phenyl and $C_{3-5}$cycloalkyl.

8. A pharmaceutical composition comprising a pain-ameliorating effective amount of a compound according to structural diagram I:

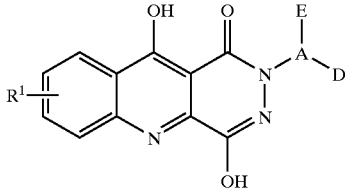

wherein:
 $R^1$ is halo;
 A is CH;
 E is selected from phenyl and $C_{3-7}$cycloalkyl;
 D is selected from pyridyl and N-oxide of pyridyl,
or tautomers or pharmaceutically-acceptable salts thereof, together with a pharmaceutically-acceptable excipient or diluent.

* * * * *